United States Patent
Karavas et al.

(10) Patent No.: US 11,154,585 B2
(45) Date of Patent: Oct. 26, 2021

(54) ORODISPERSIBLE FILM COMPOSITION COMPRISING ENALAPRIL FOR THE TREATMENT OF HYPERTENSION IN A PEDIATRIC POPULATION

(71) Applicant: PHARMATHEN S.A., Pallini-Attikis (GR)

(72) Inventors: Evangelos Karavas, Pallini Attikis (GR); Efthymios Koutris, Pallini Attikis (GR); Vasiliki Samara, Pallini Attikis (GR); Ioanna Koutri, Pallini Attikis (GR); Anastasia Kalaskani, Pallini Attikis (GR); Lida Kalantzi, Pallini Attikis (GR); Andreas Kakouris, Pallini Attikis (GR); Amalia Diakidou, Pallini Attikis (GR); George Gotzamanis, Pallini Attikis (GR); Zaharias Georgousis, Pallini Attikis (GR); Louiza Konstanti, Pallini Attikis (GR)

(73) Assignee: PHARMATHEN S.A., Pallini-Attikis (GR)

(*) Notice: Subject to any disclaimer, the term of this patent is extended or adjusted under 35 U.S.C. 154(b) by 0 days.

(21) Appl. No.: 16/942,606

(22) Filed: Jul. 29, 2020

(65) Prior Publication Data
US 2020/0360461 A1    Nov. 19, 2020

Related U.S. Application Data

(63) Continuation of application No. 15/327,078, filed on Jan. 18, 2017, now abandoned.

(51) Int. Cl.
| | | |
|---|---|---|
| *A61K 38/05* | (2006.01) | |
| *A61K 9/00* | (2006.01) | |
| *A61K 31/401* | (2006.01) | |
| *A61K 47/36* | (2006.01) | |
| *A61K 47/02* | (2006.01) | |
| *A61K 47/10* | (2017.01) | |
| *A61K 47/26* | (2006.01) | |
| *A61K 9/70* | (2006.01) | |

(52) U.S. Cl.
CPC ............ *A61K 38/05* (2013.01); *A61K 9/0056* (2013.01); *A61K 9/7007* (2013.01); *A61K 31/401* (2013.01); *A61K 47/02* (2013.01); *A61K 47/10* (2013.01); *A61K 47/26* (2013.01); *A61K 47/36* (2013.01)

(58) Field of Classification Search
None
See application file for complete search history.

(56) References Cited

U.S. PATENT DOCUMENTS

| | | | |
|---|---|---|---|
| 9,603,935 B2* | 3/2017 | Borges | .................. A61K 9/006 |
| 2003/0107149 A1 | 6/2003 | Yang | |

FOREIGN PATENT DOCUMENTS

| | | | |
|---|---|---|---|
| EP | 2732813 A1 | | 5/2014 |
| WO | WO2012-053006 | * | 4/2012 |

OTHER PUBLICATIONS

Semalty et al. ("Formulation and Evaluation of Mucoadhesive Buccal Films of Enalapril Maleate" Indian J Pharm Sci 2010; 72(5) 571-575).*
Nagar et al. (Insights into Polymers: Films Formers in Mouth Dissolving Film; Drug Invention Today, 2011,3(12), 280-289).*
Arya et al. ("Fast Dissolving Oral Films: An innovative Drug Delivery System and Dosage Form" International Journal of ChemTech Research; vol. 2(1)).*
Written Opinion of the ISR, WIPO,PCT/EP2015/001243.
Yogyata S. Pathare. et al: "Polymers Used for Fast Disintegrating Oral Films: A Review", International Journal of Pharmaceutical Sciences Review and Research, 21(1), Jul.-Aug. 2013, No. 29, pp. 169-178.

* cited by examiner

*Primary Examiner* — James H Alstrum-Acevedo
*Assistant Examiner* — Tara L Martinez
(74) *Attorney, Agent, or Firm* — AKC Patents, LLC; Aliki K. Collins

(57) ABSTRACT

The present invention relates to an oral applicable therapeutic dosage form, in particular an orodispersible film comprising Enalapril or pharmaceutically acceptable salts thereof for use in the treatment of hypertension in a pediatric population. The pediatric population is defined from 1 to 18 years of age. The present invention also provides a method of manufacturing of such a dosage form.

12 Claims, No Drawings

ORODISPERSIBLE FILM COMPOSITION COMPRISING ENALAPRIL FOR THE TREATMENT OF HYPERTENSION IN A PEDIATRIC POPULATION

CROSS REFERENCE TO RELATED CO-PENDING APPLICATIONS

This application is a continuation of U.S. application Ser. No. 15/327,078 filed Jan. 18, 2017 and entitled "ORODISPERSIBLE FILM COMPOSITION COMPRISING ENALAPRIL FOR THE TREATMENT OF HYPERTENSION IN A PEDIATRIC POPULATION", the contents of which are expressly incorporated herein by reference.

This application claims the benefit of European patent application Serial No. PCT/EP2014/002095 filed Jul. 31, 2014 and entitled "ORODISPERSIBLE FILM COMPOSITION COMPRISING ENALAPRIL FOR THE TREATMENT OF HYPERTENSION IN A PEDIATRIC POPULATION", the contents of which are expressly incorporated herein by reference.

FIELD OF THE INVENTION

The present invention relates to an oral applicable therapeutic dosage form, in particular an orodispersible film comprising Enalapril or pharmaceutically acceptable salts thereof for use in the treatment of hypertension in a pediatric population. The pediatric population is defined from 1 to 18 years of age. The present invention also provides a method of manufacturing of such a dosage form.

BACKGROUND OF THE INVENTION

Hypertension or high blood pressure is a serious health issue in many countries. Blood pressure is the product of cardiac output and peripheral vascular resistance and is created by the force exerted by the circulating blood on the walls of the blood vessels. The higher the blood pressure the harder the heart needs to work. Statistics show that 1 in 3 adults in developed countries have hypertension. If left untreated, it is considered a substantial risk factor for cardiovascular and other diseases including coronary heart disease, myocardial infarction, congestive heart failure, stroke and kidney failure. Hypertension is classified as primary or essential hypertension and secondary hypertension. Primary hypertension has no known cause and may be related to a number of environmental, lifestyle and genetic factors such as stress, obesity, smoking, inactivity and sodium intake. Secondary hypertension can be caused by drug or surgical interventions, or by abnormalities in renal, cardiovascular or the endocrine system.

In adults, hypertension is defined regardless of age, sex or body weight as blood pressure being 140/90 mm Hg or higher in stage 1 hypertension and 160/100 mm Hg or higher in stage 2 hypertension. In children, hypertension is characterized as blood pressure being between the $95^{th}$ and $99^{th}$ percentile (of the child's age, sex and height) plus 5 mm Hg in stage 1 and blood pressure above the $99^{th}$ percentile (of the child's age, sex and height) plus 5 mm Hg is characterized as stage 2 hypertension. If stage 1 is asymptomatic and without organ damage it allows time for evaluation before initiation of treatment; whereas in stage 2 prompt evaluation and treatment are required.

Hypertension in now more commonly observed in children and adolescents with a 2-9% incidence depending on age, sex and ethnicity and is associated with long term risks of ill-health. The prevalence of hypertension in children is increasing due to the rise in obesity in children. Symptoms include headache, fatigue, blurred vision, epistaxis, Bell's palsy and sleep-disordered breathing. Hypertension in children and adolescents is treated with lifestyle changes, including weight loss, a healthy, low-sodium diet, regular physical activity and avoidance of tobacco and alcohol. However, in children with symptomatic hypertension, secondary hypertension, target organ damage, diabetes or persistent hypertension should be treated with antihypertensive medications promptly. In addition, a child with blood pressure greater than or equal to $95^{th}$ percentile in a medical setting but normal pressure outside the office is said to have white coat hypertension.

In neonates hypertension is discovered on routine monitoring of vital signs. The blood pressure in infants in influenced by various factors, including birth weight, gestational age, and postconceptual age. Other presentations of neonatal hypertension to be aware of in acutely ill infants include congestive heart failure and cardiogenic shock, which are potentially life threatening but can gradually resolve with appropriate blood pressure reduction. Symptoms in infants include feeding difficulties, unexplained tachypnea, apnea, lethargy, irritability or seizures and in older infants unexplained irritability or failure to thrive may be the only manifestations.

The causes of hypertension in children and adolescents are similar to those in adults. Nevertheless, most common etiologies in children are observed in younger children rather than adolescents and in particular those with stage 2 hypertension. The younger the age of the child the higher the probability is of identifying the underline cause of stage 2 hypertension. In children under 12 years of age, renal disease and renovascular hypertension are the most common causes, followed by aortic coarctation and primary hypertension. Endocrine causes such as pheochromocytoma, primary aldosteronism and Cushing's syndrome are more rare causes. In children over 12 years of age, primary hypertension is the most common cause and is characterized by elevated systolic blood pressure or elevated systolic and diastolic blood pressure. More recently, obstructive sleep apnea has been recognized as a cause of secondary hypertension; the condition being more prevalent in obese children and adolescents.

A number of antihypertensive drugs are available for treating hypertension. The various therapeutic classes included alpha-adrenergic blockers, beta-blockers, calcium channel blockers, hypotensives, mineralcorticoid antagonists, central alpha-agonists, diuretics, and renin-angiotensin-aldosterone inhibitors which include angiotensin II receptor antagonists and angiotensin-converting enzyme inhibitors (ACE).

ACE inhibitors in particular, inhibit the angiotensin-converting enzyme which is a peptydyl dipeptidase that catalyzes angiotensin I to angiotensin II, a potent vasoconstrictor involved in regulation of blood pressure. However, the treatment of hypertension in children has proven more difficult since there are no anti-hypertensive dosage forms available, that are suitable for administration to children. Since the dosage required to treat hypertension in children is much smaller, the parent needs to use the adult drug dosage form and cut it keeping in mind the weight of the child. This can lead to miscalculations of the required dose and more importantly it can result in the parent not giving a stable dose to the child resulting in inadequate treatment. Furthermore, tablets and capsules are harder to administer to children of a younger age without causing complaining and/or emesis and therefore treatment compliance might be difficult.

Enalapril is a prodrug belonging to the ACE inhibitor medications. It is rapidly hydrolyzed in the liver to Enalaprilat following oral administration and is excreted primarily by renal excretion. In addition to treating hypertension, Enalapril has been used for treatment of symptomatic heart failure and assyptomatic left ventricular dysfunction. Its chemical name is (2S)-1-{[92S0-1-ethoxy-1-oxo-4phenylbutan-2-yl]amino}pyrrolidine-2carboxylic acid and it has a molecular weight of 376.447 g/mol. U.S. Pat. Nos. 4,374,829, 4,374,829, 4,472,380 and 4,510,083 disclose Enalapril and methods for its preparation.

Enalapril has been marketed as a tablet in its maleate salt form, however there is no available children's dosage form in the market. Enalapril maleate has a molecular weight of 492.5, it is an off-white polymorphic crystalline powder and is freely soluble in methanol and dimethylformamide, soluble in alcohol, sparingly soluble in water, slightly soluble in semi polar organic solvents and practically insoluble in nonpolar organic solvents. Enalapril maleate is a derivative of two amino acids: L-alanine and L-proline. The maleate salt of Enalapril differs structurally from Enalaprilat by the presence of an ethoxycarbonyl group rather than a carboxy group at position 1 of L-alanyl-L-proline and the presence of the maleate salt. These structural modifications result in increased absorption of Enalapril maleate at the gastrointestinal tract (GI) compared to Enalaprilat.

It is known in the art that many compounds that inhibit ACE have poor stability either in the form of free acids or salts, when they are in a pharmaceutical dosage form. These compounds easily decompose, first of all by hydrolysis and intramolecular cyclization, but the amount of other decomposition products is often not identified. This is particularly true for Enalapril and its maleate salt and it becomes clear from the prior art.

According to EP0545194 Enalapril sodium salt is more stable in pharmaceutical dosage forms than Enalapril maleate salt. Furthermore, EP0264887 suggest the use of ascorbic acid as an antioxidant or color stabilizing agent when the API is an ACE inhibitor.

In addition, U.S. Pat. No. 5,562,921 discloses that Enalapril degrades at a faster rate in the presence of some diluents namely microcrystalline cellulose, dibasic calcium phosphate, and tribasic calcium phosphate, lubricants, namely magnesium stearate and calcium stearate, and disintegrants such as crospovidone, and sodium starch glycolate. The composition disclosed was free of microcrystalline cellulose, cellulose derivatives or cellulose polymers, calcium phosphate, disintegrants, and magnesium stearate. At least 50% by weight of the pharmaceutical excipients in the composition were pharmaceutically acceptable water soluble substances such that the composition could dissolve sufficiently rapidly and not require disintegrants. Moreover, U.S. Pat. No. 4,743,450 discloses the use of stabilizers to minimize the cyclization, hydrolysis and coloration of ACE inhibitors.

Oral or orodispersible films disintegrate within seconds when placed on the tongue and because swallowing is not necessary and because it adheres to the tongue and it cannot be spat out; it is an ideal dosage form for pediatric and geriatric populations. The main idea of manufacturing is the addition of the active pharmaceutical ingredient (API) to a polymer solution which is casted, dried, cut to final size and individually packaged. To date, there is no oral film comprising Enalapril, especially an oral film targeted to the pediatric population.

The problem to be solved by the present invention is to manufacture a dosage form for the treatment of hypertension in children that is easy to swallow, it cannot be spat out, it has no risk of choking and/or aspiration, it has a pleasant taste and therefore it has increased compliance compared to other dosage forms targeting adult populations and is has an easy and cost effective manufacturing process. There still remains a need for an effective and safe anti-hypertensive treatment in children meeting all the above criteria and the objective of the present inventions is to provide such a dosage form.

SUMMARY OF THE INVENTION

The main objective of the present invention is to develop a fast disintegrating oral film comprising an anti-hypertension medication such as Enalapril or a pharmaceutically acceptable salt thereof. The fast disintegrating oral film of the present invention is suitable for administration to a pediatric population of a specific age group.

It is, therefore, an object of the present invention to provide a thermodynamically stable and efficient product in the form of a film with a reduced amount of impurities but without reduced half-life of the film; comprising Enalapril or a pharmaceutically acceptable salt thereof for the treatment of hypertension in children.

An object of the present invention is for the fast disintegrating oral film to be individually packed in different concentrations and be suitable for administration in children and adolescents of all age groups from 1 year onward. In addition, administration of the oral film can be done without water and with no risk of choking or spitting out; as such film is glued to the tongue until disintegration and swallowing.

A further approach of the present invention is to provide a dosage form with instant dissolution in the mouth and quick onset of action and a dosage form which is also amusing and easy-to-administer to children. Furthermore, the dosage form is portable and very discrete for administration to children and adolescent that will not compromise compliance.

Another object of the present invention is to provide an oral fast disintegrating film comprising Enalapril or a pharmaceutically acceptable salt thereof and a water-soluble polymer or a mixture of water-soluble polymers enabling film formation and a pH increasing agent. The oral film of the present invention can further comprise a filler, a surfactant, a plasticizer, a sweetener, a flavoring agent, a stimulating agent or combinations thereof.

A further object of the present invention is to provide a manufacturing process for the oral fast disintegrating film of the present invention comprising the following main steps:
  Weighing of raw materials
  Mixing of excipients, water and API in a high shear vacuum mixer until a homogenous casting solution is formed. The mixing step is performed under nitrogen blanketing
  The solution is casted on one side PE/silicon coated paper and dried until the film is formed
  Reels of films are converted into single dose sachets
  Sachets are packaged into laminated foil packaging (secondary packaging)

In accordance with the above objects of the present invention, the manufacturing process of the present invention is robust, cost effective and allows for customization of the dosage form.

Other objects and advantages of the present invention will become apparent to those skilled in the art in view of the following detailed description.

DETAILED DESCRIPTION OF THE INVENTION

The main object for the present invention is to provide an orodispersible film which can be administered to a pediatric population of a specific age for the treatment of hypertension, comprising Enalapril or pharmaceutically acceptable salts thereof.

For the purpose of the present invention, a pharmaceutical composition comprising an active agent or a combination of active agents is considered "stable" if said agent or combination of agents degrades less of more slowly than it does on its own or in known pharmaceutical compositions.

According to the present invention the term "orodispersible film" refers to films which can be orally administered to a patient and which disintegrates or dissolves in the oral cavity of the patient and is then swallowed for gastrointestinal absorption. Disintegration or dissolution of the film preferably results from contact with the saliva and in particular is achieved in a short period of time such as preferably below 2 minutes, more preferably below 1 minute and most preferably below 30 seconds.

Preferably, the orodispersible film is a pharmaceutical dosage form comprising at least one active pharmaceutical ingredient which is suitable for oral administration, a film-forming substance, a pH increasing agent, a sweetener and at least one additional component described below.

Examples of additional components may include, but are not limited to, additives such as thickeners, fillers, plasticizers, secondary sweetening agents, flavoring agents, acidic agents, pH adjusting agents, emulsifiers, surfactants, binders, preservatives, antioxidants, pigments, coolants and the like. Components of such additives will be described in great detail.

A "film-forming substance" according to the invention is a substance which is capable of forming a cohesive, solid or gelatinous film or layer. The film or layer in particular can be formed by casting or otherwise applying a formulation containing the film-forming substance solved or dispersed in a solvent, and optionally further ingredients onto a surface. Preferably, the film-forming substance is a polymer.

The orodispersible film of the present invention may comprise a water soluble polymer. Examples of water soluble polymers include, but are not limited to, pullulan, gelatin, pectin, low viscosity pectin, HPMC, low viscosity HPMC, hydroxyethyl cellulose, HPC, carcoxymethyl cellulose, polyvinylalcohol, polyacrylic acid, methyl methacrylate copolymer, carboxyvinyl polymer, polyethyleneglycol, alginic acid, low viscosity alginic acid, sodium alginate, modified starch, casein, whey powder extract, soy protein extract, zein, levan, elsinan, gluten, acacia gum, carrageenan, Arabic gum, guar gum, locust bean gum, xanthan gum, agar and the like.

Preferably, the water soluble polymer of the present invention may include at least one selected from the group consisting of pullulan, HPMC, HPC and modified starch or a combination thereof. Most preferably, the water soluble polymer of the present invention is a combination of pullulan and a modified starch such as Lycoat®. An amount of the water soluble polymer combination in the orodispersible film may range from 40 to 90% w/w, preferably 50 to 80% w/w, and more preferably 55 to 75% w/w of the film. The ratio of pullulan to the modified starch is from 1:1 to 1:2, and more preferably from 1:1.5.

Fillers may be added as a film component to reduce greasy features of the film in the mouth and endow a skeleton structure to the film. In addition, a filler can control the film disintegration time, drug elution rate and the stickiness of the film. Fillers may include at least one selected from the group consisting of microcrystalline cellulose (MCC), cellulose polymer, magnesium carbonate, calcium carbonate, limestone powder, silicate, clay, talc, titanium dioxide, and calcium phosphate. The amount of the filler may range from 1 to 15% w/w of the film.

A plasticizer may be used to improve the flexibility of the film. The plasticizer may be one selected from the group consisting of sorbitol, maltitol, xylitol, glycerol, polyethyleneglycol, propyleneglycol, hydrogenated starch syrup, starch syrup, triacetin, glycerol oleate, glycerol, sucrose fatty acid ester and double chain fatty acid. Preferably, the plasticizer used in the present invention is glycerol. The amount of the plasticizer may range from 0.1 to 15% w/w of the film, preferably from 3 to 13% w/w of the film and more preferably from 5 to 10% w/w of the film.

The orodispersible film of the present invention may include a sweetening agent for a more pleasant taste; the sweetener may be at least one selected from the group consisting of sucrose, glucose, maltose, sucralose, oligosaccharides dextrin, alpha cyclodextrin, beta cyclodextrin, gamma cyclodextrin, methyle beta cyclodextrin, cluster dextrin, invert sugar, fructose, lactose, galactose, starch syrup, sorbitol, maltilol, xylitol, erythritol, hydrogenated starch syrup, mannitol, trehalose. Preferably, the orodispersible film of the present invention comprises sucralose. The amount of the sweetener can range from 0.1 to 10% w/w of the film, preferably from 3 to 8% w/w of the film, more preferably from 4 to 7% w/w of the film.

The film may further include an acidic agent. The acidic agent serves to control taste together with the sweetener and in addition, to stimulate secretion of saliva in order to dissolve the orodispersible film. The acidic agent may be at least one selected from the group consisting of citric acid, malic acid, fumaric acid, tartaric acid, ascorbic acid, succinic acid, adipic acid, lactic acid. The amount of the acidic agent can range from 0.1 to 10% w/w of the film.

Furthermore, the orodispersible film of the present invention may comprise a flavoring agent such as a natural flavor, an artificial flavor or a mixture thereof. The natural flavor may include aromatic plants, especially extracts and/oils obtained from leaves, flowers or fruits of such plants and can include spearmint oil, cinnamon oil, peppermint oil, lemon, oil, clove oil, bay oil, thyme oil, nutmeg oil, sage oil, almond oil and the like. The artificial flavoring may include synthetic fruit flavors such as lemon, orange, grape, lime, strawberry, etc and other synthetic flavors such as vanilla, chocolate, coffee, cocoa, ginseng, citrus etc. The amount of the flavoring agent can range from 1 to 15% w/w of the film.

Surfactants such as emulsifiers, foaming agents, detergents or dispersants can be added to the orodispersible film composition of the present invention. Surfactants may include, but are not limited to glycerol fatty acid ester, sucrose fatty acid ester, lecithin, enzyme treated lecithin, polysorbates, sorbitan fatty acid ester and propylene glycol. The amount of the surfactant may depend on the kind or the amount of oils present in the composition and can range from 0.1 to 10% w/w of the film. For the purpose of the present invention the suitable surfactant is polysorbate 80, such as Tween® 80 in an amount from 0.1 to 10% w/w of the film, preferably from 2 to 8% w/w of the film, more preferably from 4 to 6% w/w of the film.

The orodispersible film of the present invention may also comprise an antioxidant in order to minimize degradation of Enalapril. Suitable antioxidants include chelating agents, such as ethylenediaminetetraacetic acid (EDTA), ethylene glycol tetraacetic acid (EGTA), sodium bisulfite, sodium metabisulfite, ascorbic acid, ascorbyl palmitate and tocopherols such as alpha-tocopherol, beta-tocopherols, gamma-tocopherols, delta-tocopherols, tocopherol acetate, tocotrienols or combinations thereof. The suitable amount of an antioxidant can range from 0.1 to 5% w/w of the total weight of the film.

The orodispersible film of the present invention may include an appropriate pigment such as natural and/or synthetic pigment in an amount from 0.01% to 10% w/w of the film.

The orodispersible film of the present invention may further include a cooling agent. The cooling agent can be selected from the group consisting of WS3, SW23 or questive-L in an amount ranging from 0.01 to 5% w/w of the film.

Manufacturing of orodispersible films is done by various techniques such as solvent casting, hot-melt extrusion, semi-solid casting, solid-dispersion extrusion and rolling. The present invention is manufactured using the solvent casting technique because the process is very straight forward and cost effective and can be as competitive as tableting regarding cost and time of manufacturing. In the solvent casting method the water-soluble ingredients are dissolved to form a clear, viscous solution. The API and other pharmaceutically acceptable excipients are also dissolved in the aqueous, viscous solution. The entrapped air is removed by vacuum for uniform film properties and thickness. The resulting solution is cast as film, allowed to dry, and cut to the desired size. The properties of the API play a critical role in the selection of the suitable solvent and the film forming excipients. The cut film is packaged in single sachets.

More particularly, the process for the manufacturing of the orodispersible film of the present invention can be summarized in the following steps:

Dispensing and weighing raw materials;

Mixing Enalapril maleate, the combination of water-soluble polymers, the pH adjusting agent, the surfactant, the plasticizing agent, the sweetener and water under a nitrogen blanketing in a vacuum mixer until a homogenous casting solution has been formed;

Casting the solution on one sided PE/silicon coated paper and drying the solution at 40.degree. C. for 4 hours;

Cutting and converting reels of film into single dose sachets;

Packaging sachets into a secondary laminated foil packaging with a different color according to dosage strength.

The orodispersible film has a thickness of from 20 to 700 .mu.m, preferably from 40 to 400 μm and more preferably from 65 to 100 μm, and a weight of from 5 to 500 mg, preferably from 10 to 300 mg and more preferably from 20 to 150 mg. The shape of the oral film may be common shape such as rectangle, square, circle and an ellipse.

In addition, the size of the orodispersible film of the present invention is from 1 to 10 $cm^2$. The manufacturing process of the present invention has additional advantages over other processes because more than one dosage strength can be prepared from the same reel of film depending on the size of the film. This finding significantly decreases the cost of manufacturing.

The preferred form of Enalapril is Enalapril maleate. Surprisingly, the orodispersible film of the present invention is stable and Enalapril maleate impurities were kept to a minimum. The orodispersible films will be produced with various dosages of Enalapril maleate and will be suitable for administration to all children and adolescents from the age of 1 year to the age of 18 years. The various concentrations include 1.25 mg, 2.5 mg, 5 mg, 10 mg and 20 mg Enalapril maleate per orodispersible film. Moreover, the different strengths will be package into different color sachets to avoid any risk of a dosing error. The different strengths will be able to cover all doses from 0.08 to 0.50 mg/Kg administered depending on the child's weight. More preferably, the dose will be from 0.1 mg/kg to 0.42 mg/Kg once daily.

A surprise finding of the present invention was that the stability of the active ingredient was significantly improved by increasing the pH of the casting solution using an alkaline or basic agent. Furthermore the stability of Enalapril depended more on the increase of the pH rather than the addition of an antioxidant. Another important finding was that the increase of the pH also significantly improved the relative humidity and the disintegration time of the dried film.

Any edible or pharmaceutically acceptable pH increasing agent such as an alkaline or basic agent may be used to increase the pH to the optimum range. pH increasing agents may be selected from the group consisting of hydroxides, edible carbonates, edible bicarbonates, basic amino acids, buffers and mixtures thereof. Suitable hydroxides include sodium hydroxide, calcium hydroxide, magnesium hydroxide and mixtures thereof. Suitable edible carbonates include alkali metal carbonates, such as calcium carbonate, sodium carbonate and potassium carbonate. Edible bicarbonates include alkali metal carbonates, such as sodium bicarbonate and potassium bicarbonate. Basic amino acids include lysine and arginine. Buffers include sodium citrate buffers and potassium citrate buffers. Preferably the pH increasing agent used in the present invention is sodium hydroxide (NaOH). The amount of NaOH in the orodispersible film may range from 0.1 to 5% w/w of the total weight of the film, preferably from 0.5 to 4.5% w/w of the total weight of the film, and more preferably from 1.0% to 4% w/w of the total weight of the film. The optimum pH range is from 6.0 to 7.0, preferable from 6.3 to 6.7 and more preferably is 6.4 to 6.5.

The orodispersible film of the present invention has many advantages of other dosage forms targeting the pediatric population. First of all, the dosage form is age appropriate for swallowing the film once dispersed without the risk of choking or aspiration for all children and adolescents over the age of 1 year. The film is glued to the tongue during the time it disperses therefore the risk of choking and spiting the medication are significantly reduced for all ages. Further advantages of the orodispersible film of the present invention include that the film can be portable and can be administered without drinking water; therefore the administration can be discrete and convenient especially for the adolescent population. So, the orodispersible film of the present invention can be administered in a discrete manner, it requires no lifestyle changes, it takes into account all the behavioral characteristics of the age group, especially adolescents, and therefore will have increased treatment compliance.

The present invention will be described in greater detail by the following examples. However, these examples are intended for illustrative purposes and it will be appreciated by a person skilled in the art that these examples do not restrict the scope of the present invention in any way.

EXAMPLES

Example 1

A number of different polymers were considered as the film-forming substance of the present invention. Polymers tested included pullulan, modified starch such as Lycoat®, hydroxypropylmethyl cellulose, hydroxypropyl cellulose (HPC), HPC LF and HPC F and combinations thereof. Surprisingly, and based on results of homogeneity and viscosity of the casting liquid the best film-forming substance was a combination of two polymers pullulan and Lycoat®.

The next step was to develop different formulations comprising combinations of pullulan and Lycoat® and further pharmaceutically acceptable excipients. Sixteen different formulations were developed comprising the different combinations of pullulan and Lycoat® and further comprising microcrystalline cellulose 102 (MCC 102) as a filler, glycerol as a plasticizing agent, sucralose as a sweetener, citric acid as a saliva stimulating agent and Tween®80 as a surfactant. A screening design of the sixteen different formulations was performed where the factors were the excipients and the responses were the physicochemical properties of the casting liquid and the film. The following parameters were measured for the casting liquid: viscosity and pH; and for the film: thickness, disintegration, Karl Fisher, and their appearance and brittleness. All the experiments were done for 50 ml casting liquid, a 10 mg strength film as a 2×2 cm size and the film was 0.5 mm thick before drying. The film drying conditions were 25° C. (RT); overnight. The results were collected and the optimum formulation was determined to be the following: 10 mg/film Enalapril maleate, 20 mg/film pullulan, 20 mg/film Lycoat®, 18.16 mg/film MCC 102, 5 mg/film glycerol, 2 mg/film citric acid, 4 mg/film Tween80® and 10 mg/film sucralose. The physicochemical characteristics of the formulation were: casting liquid viscosity: 3250 cP and casting liquid pH: 2.47; and film thickness: 0.20-024 mm (after drying), film disintegration time: 19 seconds, Karl Fisher: 3.681, brittleness: not brittle (difficult to handle).

Stability studies were performed at various conditions (5° C.; 25° C.; 30° C.; 40° C.) and impurities (C, B, H, D) were measured. The results showed an increase in impurity D that could be due to oxidation.

Example 2

An increase of impurities was detected in the formulation of example 1; therefore different modifications were necessary to improve the formulation. An antioxidant factor was deemed necessary and was added to the formulation and in addition the mixing procedure was performed under nitrogen blanketing in order to avoid possible oxidation of Enalapril. Furthermore, the amount of water-soluble polymers was increased to optimize viscosity and film formation, which was used as the blank trial of example 2. Different antioxidants were also tested which were tocoferole, EDTA and a combination thereof. The formulations tested are shown in Table 1. The physicochemical properties of the casting liquids from the formulations were measured and the results are also shown in Table 1. The casting liquid was dried and the formed film was cut in dimension 2.times.2 cm for dosage strength of 10 mg Enalapril per film. The physicochemical characteristics of the film were measured and the results are also show in Table 1.

TABLE 1

Formulations prepared with and without (blank trial) antioxidants. Shown are viscosity and pH measurements of the casting liquid and disintegration time, Karl Fisher measurements for the dried film according to the formulations of example 2.

|  | Blank Trial Mg/film | Trial 2 Mg/film | Trial 3 Mg/film | Trial 4 Mg/film |
|---|---|---|---|---|
| API | 15 | 15 | 15 | 15 |
| Pullulan | 30 | 30 | 30 | 30 |
| MCC | 20 | 20 | 20 | 20 |
| Glycerol | 5 | 5 | 5 | 5 |
| Lycoat ® | 45 | 45 | 45 | 45 |
| Citric Acid | 1 | 1 | 1 | 1 |
| Tween ® 80 | 3 | 3 | 3 | 3 |
| dla-tocoferole | — | 0.1 | — | 0.05 |
| EDTA | — | — | 0.1 | 0.05 |
| Sucralose | 10 | 10 | 10 | 10 |
| Viscosity (cP) | 5488 | 6450 | 5100 | 4300 |
| pH | 2.47 | 2.47 | 2.48 | 2.46 |
| Film thickness | 0.22-0.25 | 0.26 | 0.25 | 0.24 |
| Disintegration (sec) | 40 | 75 | 38 | 52 |
| Karl Fisher (%) | 9.34 | 5.223 | 4.714 | 6.188 |

Extensive stability studies were performed for the film formulations of example 2. For the stability studies the impurities C, B, H, D were measured at various conditions and an argon atmosphere (25° C.; 30° C.; 40° C.; different Relative Humidity). The results are shown in the Tables below.

TABLE 2

Stability studies for the film formulations of Example 2 at Time 0 (T = 0)

|  | HOMOGENIZED BULK SAMPLES | | | |
|---|---|---|---|---|
| T = 0 | Blank Trial | Trial 2 | Trial 3 | Trial 4 |
| Impurity C | 0.12 | 0.13 | 0.12 | 0.11 |
| Impurity B | — | — | — | — |
| Impurity H | 0.05 | 0.05 | 0.05 | 0.04 |
| Impurity D | 0.04 | 0.09 | 0.04 | 0.04 |
| Total | 0.21 | 0.27 | 0.21 | 0.19 |

TABLE 3

Stability studies for the film formulations of Example 2 at Time after 15 days (T = 15 days) and in an argon atmosphere at 25° C. and 60% Relative Humidity

| T = 15 days | ENALAPRIL FILM 25° C./60% RH | | | |
|---|---|---|---|---|
|  | Blank Trial | Trial 2 | Trial 3 | Trial 4 |
| Impurity C | 0.24 | 0.31 | 0.25 | 0.26 |
| Impurity B | — | — | — | — |
| Impurity H | 0.05 | 0.05 | 0.05 | 0.05 |
| Impurity D | 0.75 | 0.85 | 0.76 | 0.89 |
| Total | 1.04 | 1.21 | 1.06 | 1.20 |

TABLE 4

Stability studies for the film formulations of Example 2 at Time after 15 days (T = 15 days) and in an argon atmosphere at 30° C. and 75% Relative Humidity

| T = 15 days | ENALAPRIL FILM 30° C./75% RH | | | |
|---|---|---|---|---|
|  | Blank Trial | Trial 2 | Trial 3 | Trial 4 |
| Impurity C | 0.38 | 0.46 | 0.35 | 0.45 |
| Impurity B | — | — | — | — |
| Impurity H | 0.05 | 0.05 | 0.05 | 0.05 |
| Impurity D | 1.7 | 1.9 | 1.5 | 2.3 |
| Total | 2.13 | 2.41 | 1.90 | 2.80 |

TABLE 5

Stability studies for the film formulations of Example 2 at Time after 15 days (T = 15 days) and in an argon atmosphere at 40° C. and 75% Relative Humidity

| T = 15 days | ENALAPRIL FILM 40° C./75% RH | | | |
|---|---|---|---|---|
|  | Blank Trial | Trial 2 | Trial 3 | Trial 4 |
| Impurity C | 0.75 | 0.92 | 0.82 | 0.87 |
| Impurity B | — | — | — | — |
| Impurity H | 0.05 | 0.05 | 0.05 | 0.05 |
| Impurity D | 5.7 | 6.8 | 4.2 | 7.4 |
| Total | 6.50 | 7.77 | 5.07 | 8.32 |

According to the data from the stability studies the formulation comprising EDTA (Trial 3) showed consistently lower levels of impurities.

Example 3

The formulation of Trial 3 from example 2 was studied further in order to evaluate the most suitable drying process. The criteria important for evaluating the drying process are the relative humidity of the final film formulation and avoiding degradation of Enalapril.

Three drying processes were tested: freeze drying, oven drying at 40° C. and hot air room drying at up to 40° C. for 18 hrs. 200 ml of the casting liquid of an improved Trial 3 formulation from Example 2 were prepared. The formulation prepared is shown in the table below (Trial 5):

TABLE 6

Trial 5 formulation of Example 3

|  | Trial 5 (200 ml) Mg/film |
|---|---|
| API | 15 |
| Pullulan | 30 |
| MCC | 30 |
| Glycerol | 14.7 |
| Lycoat ® | 40 |
| Citric Acid | 3 |
| Tween ® 80 | 6 |
| EDTA | 0.04 |
| Sucralose | 22.5 |
| Viscosity (cP) | 4235 |
| pH | 2.47 |

The casting liquid was dried using the three different drying techniques mentioned above and cut in a 2×2 dimension with the dosage strength of 10 mg per film. The dried films were then tested for their disintegration time and the results were compared. Films dried with the freeze drying technique were too brittle; therefore this technique was excluded as an option. The oven drying technique and hot air room technique were further examined to define the most suitable drying time for the film.

Further experiments were performed to determine the appropriate drying time and three time points were used: 3 hrs, 4 hrs, and 24 hrs. An experiment was performed, wherein the humidity of the casting liquid formulation of Trial 5 was measured during drying and the results are shown to the tables below (Table 7).

TABLE 7

Humidity measurements for the formulation of Trial 5 after drying.

| 40° C. oven | | Hot air room 40° C. | |
|---|---|---|---|
| Karl Fisher | % | Karl Fisher | % |
| 3 hrs | 13.046 | 3 hrs | 10.999 |
| 4 hrs | 2.209 | 4 hrs | 2.430 |
| 24 hrs | 3.110 | 24 hrs | 5.184 |

The results clearly demonstrate that the time limit of 4 hrs is the optimum for film drying as at 3 hrs the humidity of the film is too high and at 24 hrs drying there is no added benefit or the humidity levels are worse. Drying at 40° C. in an oven seems to have consistently better results over drying in a hot air room. Oven drying is also suitable for large scale production; it is simple and has no additional costs of manufacturing. However, hot air room drying could also be a suitable option. Finally, drying at a higher temperature would not be indicated because the amount of impurities of Enalapril would increase.

Example 4

Although the drying process was optimized, the stability issue still exists and further optimization of the formulation is necessary. In order to increase the pH of the casting liquid and reduce the amount of impurities, citric acid was excluded from the formulation and in addition sodium oxide 10N solution (NaOH) was used. A range of pH values were tested with and without the antioxidant agent. 50 ml batches were prepared and oven dried for 4 hours at 40° C. with average viscosity 9750 cP. The batches named Trial 6, 7, 8, 9 are shown in Table 8. The dried films were cut in 2X2 cm dimensions for a 10 mg dosage strength and a thickness of 0.20-0.25 mm and the physicochemical characteristics of the films; relative humidity and disintegration time, were also measured (Table 8).

TABLE 8

Formulations prepared according to example 4 and physicochemical characteristics of the films produced.

|  | Trial 6 Mg/film | Trial 7 Mg/film | Trial 8 Mg/film | Trial 9 Mg/film |
|---|---|---|---|---|
| API | 3.75 | 3.75 | 3.75 | 3.75 |
| Pullulan | 7.50 | 7.50 | 7.50 | 7.50 |
| MCC 102 | 7.50 | 7.50 | 7.50 | 7.50 |
| Glycerol | 3.68 | 3.68 | 3.68 | 3.68 |
| Lycoat ® | 10 | 10 | 10 | 10 |
| Tween ® 80 | 1.5 | 1.5 | 1.5 | 1.5 |
| EDTA | 0.10 | 0.10 | — | — |
| Sucralose | 5.63 | 5.63 | 5.63 | 5.63 |
| NaOH 10N(ml) | 1.00 | 1.80 | 1.80 | 2.30 |
| pH | 5 | 6 | 6 | 6.8 |
| Karl Fisher (%) | 6.186 | 6.488 | 5.812 | 5.812 |
| Disintegration (sec) | 20-25 | 31-41 | 17-25 | 18-23 |

Comparing the results between the formulations of Trial 7 and Trial 8 which both have pH 6.0 it becomes apparent that the relative humidity and the disintegration time are better without EDTA, suggesting that the pH of the film is more important for humidity and disintegration time of the film than the use of an antioxidant. In addition, when comparing formulations Trial 8 and Trial 9, we can conclude that there is no difference in relative humidity in the range of pH between 6.0-6.8. Furthermore, all formulations of example 4 were tested in a stability study. The results are shown in the tables below.

TABLE 9

Stability studies for the film formulations of Example 4 at Time 0 (T = 0)

| | HOMOGENIZED BULK SAMPLES | | | |
|---|---|---|---|---|
| T = 0 | Trial 6 | Trial 7 | Trial 8 | Trial 9 |
| Impurity C | 0.20 | 0.20 | 0.17 | 0.18 |
| Impurity B | — | — | — | — |
| Impurity H | 0.05 | 0.05 | 0.05 | 0.05 |
| Impurity D | 0.17 | 0.07 | 0.05 | 0.04 |
| Total | 0.42 | 0.32 | 0.27 | 0.27 |

From the studies we can conclude that an increase of the pH has a significant effect in the stability of Enalapril at 40° C., suggesting that a pH range from 6.0 to 7.0, preferable from 6.3 to 6.7 and more preferably is 6.4 to 6.5 is optimum and is more important than the presence of an antioxidant in the formulation. Taken together with results from the stability studies of example 2, the findings clearly demonstrate that a pH value from 6.0 to 7.0 is stabilizing Enalapril and decreases the amounts of impurities and is more important than addition of an antioxidant.

Example 5

At this point of the development of the orodispersible film formulation and according to prior art documents regarding stability of Enalapril it was decided to exclude microcrystalline cellulose 102 (MCC 102) in order to see further improvement in the stability of the API and appearance of the film.

The main goal of the present invention is to produce orodispersible films comprising Enalapril with a simple casting technique that have a competitive cost of manufacturing. In order to keep the manufacturing cost low it was decided to try and produce a casting liquid formulation that when dried it could produce different dosage strengths according to the thickness and the dimension of the final film formulation. Keeping in mind the fact that the final volume of the casting solution would increase due to the addition of solids in the water and in addition the thickness of the film is decreased during drying thus the final concentration of Enalapril is changing during development; the amount of Enalapril in the formulation was significantly increased to a concentration of 75 mg/ml. Furthermore, the concentration of NaOH was increased to maintain the pH at the optimum value of 6.4 and it was used in the form of pellets for weighing purposes. The combination of the water-soluble polymers was also increased to achieve a higher viscosity. The following two formulations Trial 10 and Trial 11 with a different ratio of pullulan to Lycoat® from 1:1.3 to 1:1.5 were developed and are shown in Table 11. The properties of the casting liquid were determined, including specific gravity, total mass, theoretical volume, concentration of the API, viscosity and pH and results are shown (Table 11).

TABLE 10

Stability studies for the film formulations of Example 4 at Time after 1 month and in an argon atmosphere at different temperatures and relative humidity: 25° C. and 60% RH; 30° C. and 75% RH, 40° C. and 75% RH.

| | ENALAPRIL FILM | | | | | | | | | | | |
|---|---|---|---|---|---|---|---|---|---|---|---|---|
| | Trial 6 | | | Trial 7 | | | Trial 8 | | | Trial 9 | | |
| T = 1 month | 25° C. | 30° C. | 40° C. | 25° C. | 30° C. | 40° C. | 25° C. | 30° C. | 40° C. | 25° C. | 30° C. | 40° C. |
| Impurity C | 0.25 | 0.64 | 1.10 | 0.40 | 0.80 | 2.00 | 0.40 | 0.80 | 0.01 | 2.80 | 2.90 | 4.30 |
| Impurity B | — | — | — | — | — | 0.01 | — | — | 0.05 | — | — | — |
| Impurity H | 0.05 | 0.05 | 0.04 | 0.07 | 0.06 | 0.05 | 0.07 | 0.06 | 0.05 | 0.06 | 0.07 | 0.06 |
| Impurity D | 0.66 | 2.00 | 7.80 | 0.54 | 1.30 | 4.70 | 0.54 | 1.30 | 4.70 | 0.08 | 0.18 | 0.36 |
| Total | 0.96 | 2.69 | 8.94 | 1.01 | 2.16 | 6.76 | 1.01 | 2.19 | 6.76 | 2.94 | 3.15 | 4.72 |

TABLE 11

Formulations prepared according to example 5.
Shown are properties of the casting liquid.

| Mg/200 ml | Trial 10 | Trial 11 |
|---|---|---|
| Purified water | 200.00 | 200.00 |
| API | 20.00 | 20.00 |
| Pullulan | 22.00 | 23.00 |
| Lycoat ® | 30.00 | 34.00 |
| Glycerol | 10.31 | 10.31 |
| Tween ® 80 | 4.50 | 4.50 |
| Sucralose | 5.00 | 5.00 |
| NaOH (pellets) | 4.10 | 4.10 |
| Total Solids | 95.91 | 100.91 |
| Specific gravity | 1.123 | 1.124 |
| Total Mass | 295.90 | 300.90 |
| Theoretical Volume | 263.60 | 267.70 |
| Concetration API (mg/ml) | 75.87 | 74.72 |
| Viscosity | 1045.00 | 1775.00 |
| pH | 6.37 | 6.38 |

The formulations of Trial 10 and Trial 11 were cast with different thickness (0.30 mm, 0.50 mm and 0.75 mm) and dried in an oven at 40° C. for 4 hours. Next, the produced films were cut at dimensions 2×2 mm and the physicochemical properties of the films are presented in Table 12.

TABLE 12

Physicochemical characteristics of formulations of Example 5.

| | Trial 10 | | Trial 11 | |
|---|---|---|---|---|
| | Expected | Actual | Expected | Actual |
| Concentration (mg/ml) 0.30 mm Film casting | 8.97 | 4.74 | 8.97 | 4.66 |
| Concentration (mg/ml) 0.50 mm Film casting | 14.94 | 9.39 | 14.94 | 8.79 |
| Concentration (mg/ml) 0.75 mm Film casting | 22.42 | 15.99 | 22.42 | 10.84 |
| Weight (%) 0.30 mm Film dried | 52.02 | | 51.97 | |
| Weight (%) 0.50 mm Film dried | 61.88 | | 58.83 | |
| Weight (%) 0.75 mm Film dried | 70.24 | | 48.34 | |
| Thickness (mm) 0.30 mm Film dried | 0.02-0.03 | | 0.04-0.06 | |
| Thickness (mm) 0.50 mm Film dried | 0.05-0.08 | | 0.07-0.11 | |
| Thickness(mm) 0.75 mm Film dried | 0.13-0.17 | | 0.11-0.13 | |
| Disintegration (sec) 0.30 mm Film dried | 8.67 | | 6.67 | |
| Disintegration (sec) 0.50 mm Film dried | 20.33 | | 18.33 | |
| Disintegration (sec) 0.75 mm Film dried | 42.33 | | 42.00 | |

Films cast at a thickness of 0.30 mm were too brittle to handle after drying, while films cast at thickness 0.75 mm were lightly sticky after drying; in addition disintegrations times were not optimum. Therefore it was decided that the optimum casting thickness is 0.50 mm. The films produced with the slightly higher pullulan to Lycoat® ratio of 1:1.5 show slightly better physicochemical characteristics. Therefore the films produced with the formulation of Trial 11 and a thickness of 0.50 mm were further tested in stability studies for 1 month and 6 months under various conditions and the results are shown in the tables below.

TABLE 13

Stability studies for the film formulations of Example 5 at Time 0 (T = 0)

| | HOMOGENIZED BULK SAMPLES | |
|---|---|---|
| T = 0 | Trial 10 | Trial 11 |
| Impurity C | 0.21 | 0.19 |
| Impurity B | 0.03 | 0.03 |
| Impurity H | 0.05 | 0.04 |
| Impurity D | 0.05 | 0.04 |
| Total | 0.34 | 0.30 |

TABLE 14

Stability studies for the film formulation of Trial 11 and casting thickness 0.50 mm at Time after 1 month in an argon atmosphere at different temperatures and different relative humidity.

| | ENALAPRIL FILM Trial 11 | | |
|---|---|---|---|
| T = 1 month | 25° C./60% RH | 30° C./75% RH | 40° C./75% RH |
| Impurity C | 0.59 | 0.78 | 0.82 |
| Impurity B | — | — | — |
| Impurity H | 0.04 | 0.05 | 0.05 |
| Impurity D | 0.25 | 0.48 | 0.54 |
| Unknown | 0.19 | 0.31 | 0.50 |
| Total | 1.07 | 1.62 | 1.91 |

TABLE 15

Stability studies for the film formulation of Trial 11 and casting thickness 0.50 mm at Time after 6 months and in an argon atmosphere at different temperatures and different relative humidity

| | ENALAPRIL FILM Trial 11 | | |
|---|---|---|---|
| T = 6 month | 25° C./60% RH | 30° C./75% RH | 40° C./75% RH |
| Impurity C | 1.00 | 1.90 | 2.20 |
| Impurity B | — | — | — |
| Impurity H | 0.06 | 0.06 | 0.06 |
| Impurity D | 0.49 | 1.30 | 1.40 |
| Unknown | 0.58 | 1.10 | 1.50 |
| Total | 2.13 | 4.36 | 5.16 |

Example 6

The results from Trial 11 formulation were satisfactory; it was therefore decided to prepare a large scale production formulation. The following adjustments were made to optimize the formulation for the new equipment. The amount of water was reduced by 35% to achieve a suitable viscosity for coating and to decrease the elastic nature of films, the glycerol content was reduced to 6.3% (w/w dry) and the concentration of Enalapril was adjusted to 20.8% w/w (dry). All the adjustments were made keeping in mind that one casting solution can prepare all dosage strengths and the formulation is shown in the table below (Table 16).

TABLE 16

Formulation prepared according to example 6

| | Trial 12 % w/w |
|---|---|
| API | 20.80 |
| Pullulan | 23.70 |
| Glycerol | 6.27 |
| Lycoat ® | 35.06 |
| Tween ® 80 | 4.76 |
| Sucralose | 5.15 |
| NaOH pellets | 4.27 |
| Water | 1.44 water:1 solids |
| Total solids | 100.01 |

The relationships between film dimensions, weight and API concentration were assessed and an appropriate casting thickness was selected for all dosage strengths. The physicochemical properties of all dosage strengths are presented in the table below (Table 17).

TABLE 17

Characteristics of Trial 12 formulation for all dosage strengths.

| | 1.25 mg | 2.5 mg | 5 mg | 10 mg | 20 mg |
|---|---|---|---|---|---|
| Dimensions (mm) | 10 × 10 | 10 × 20 | 15 × 15 | 30 × 15 | 30 × 30 |
| Thickness (mm): | 0.072 | 0.074 | 0.077 | 0.076 | 0.084 |
| Weight (mg): | 9.79 | 21 | 25.08 | 52.41 | 114.02 |
| Disintegration (sec): | 23 | 27 | 20 | 22 | 26.5 |
| Hardness peak load(g): | 79 | 80 | 583 | 576 | 406.5 |
| Tension peak load(g): | 150 | 123 | 1105 | 1295.5 | 1156.5 |

The results show very good characteristics for the films with 5 mg, 10 mg and 20 mg dosage strengths; however the films with dosage strengths 1.25 mg and 2.5 mg were brittle and difficult to manage during the manufacturing process both at the step of casting the film and the step of cutting. This also was proved by measuring the mechanical properties of the strips. The value peak load for Hardness and Tension was quite low compared to other products available in the market. Also the final dimensions were too small for the caregiver to handle properly. The films with dosage strengths 5 mg, 10 mg, and 20 mg were studied extensively with stability studies for 6 months at various conditions. The results are shown in the tables below.

TABLE 18

Stability studies in an argon atmosphere for the film formulations of Trial 12 at Time 0 (T = 0)

| | HOMOGENIZED BULK SAMPLES Trial 12 | | |
|---|---|---|---|
| T = 0 | 5 mg | 10 mg | 20 mg |
| Impurity C | 0.28 | 0.39 | 0.44 |
| Impurity B | — | — | — |
| Impurity H | 0.05 | 0.05 | 0.05 |
| Impurity D | 0.10 | 0.07 | 0.07 |
| Unknown | 0.25 | 0.25 | 0.25 |
| Unknown | 0.04 | 0.05 | 0.06 |
| Total | 0.72 | 0.80 | 0.9 |

TABLE 19

Stability studies in an argon atmosphere for the film formulations of Trial 12 at Time 6 months in the following conditions: 25° C. and 60% RH; 30° C. and 75% RH, 40° C. and 75% RH.

| | ENALAPRIL FILM Trial 12 | | | | | | | | |
|---|---|---|---|---|---|---|---|---|---|
| | 5 mg | | | 10 mg | | | 20 mg | | |
| T = 6 months | 25° C. | 30° C. | 40° C. | 25° C. | 30° C. | 40° C. | 25° C. | 30° C. | 40° C. |
| Impurity C | 0.69 | 1.0 | 0.99 | 0.78 | 1.10 | 1.30 | 2.40 | 2.80 | 1.90 |
| Impurity B | — | — | — | — | — | — | — | — | — |
| Impurity H | 0.05 | 0.05 | 0.05 | 0.05 | 0.05 | 0.05 | 0.05 | 0.05 | 0.05 |

TABLE 19-continued

Stability studies in an argon atmosphere for the film formulations of Trial 12 at Time 6 months in the following conditions: 25° C. and 60% RH; 30° C. and 75% RH, 40° C. and 75% RH.

| | ENALAPRIL FILM Trial 12 | | | | | | | | |
|---|---|---|---|---|---|---|---|---|---|
| | 5 mg | | | 10 mg | | | 20 mg | | |
| T = 6 months | 25° C. | 30° C. | 40° C. | 25° C. | 30° C. | 40° C. | 25° C. | 30° C. | 40° C. |
| Impurity D | 0.37 | 0.50 | 0.54 | 0.31 | 0.44 | 0.47 | 0.41 | 0.28 | 0.69 |
| Unknown | 0.22 | 0.35 | 0.35 | 0.22 | 0.35 | 0.40 | 0.26 | 0.40 | 0.44 |
| Unknown | — | — | — | — | — | — | — | — | — |
| Total | 1.33 | 1.9 | 1.93 | 1.36 | 1.94 | 2.22 | 3.12 | 3.53 | 3.08 |

Taken together all the data the formulation of Trial 12 is the optimum for production of films with 5 mg, 10 mg and 20 mg strengths.

Example 7

To further optimize the film formulation for strengths of 1.25 mg and 2.5 mg another Trial was performed with the same batch size and only minor changes of formulation shown in the table below (Table 20). The film was dried and cut according to dosage strength and the physicochemical properties of the films are presented in the table below (Table 21).

TABLE 20

Formulation prepared according to example 7.

| | Trial 13 % w/w |
|---|---|
| API | 6.06 |
| Pullulan | 29.16 |
| Glycerol | 9.35 |
| Lycoat ® | 42.15 |
| Tween ® 80 | 5.71 |
| Sucralose | 6.35 |
| NaOH pellets | 1.21 |
| Water | 1.76 water:1 solids |
| Total solids | 100.01 |

TABLE 21

Characteristics of Trial 13 formulation.

| | 1.25 mg | 2.5 mg |
|---|---|---|
| Dimensions (mm) | 15 × 15 | 15 × 30 |
| Thickness (mm): | 0.058 | 0.059 |
| Weight (mg): | 22.21 | 44.22 |
| Disintegration (sec): | 23 | 27 |
| Hardness peak load(g): | 200 | 203 |
| Tension peak load(g): | 619 | 512 |

The results show that the Hardness and Tension measurements for the 1.25 mg and 2.5 mg strength films were significantly improved. In addition, the appearance and the brittleness of the films were also improved. Therefore it was decided to perform stability studies for the films of those two strengths for 6 months and the results are shown in the tables below.

TABLE 22

Stability studies in an argon atmosphere for the film formulations of Trial 13 at Time 0 (T = 0)

| | HOMOGENIZED BULK SAMPLES Trial 13 | |
|---|---|---|
| T = 0 | 1.25 mg | 2.5 mg |
| Impurity C | 0.67 | 0.65 |
| Impurity B | — | — |
| Impurity H | 0.05 | 0.05 |
| Impurity D | 0.12 | 0.12 |
| Unknown | 0.22 | 0.22 |
| Unknown | — | — |
| Total | 1.06 | 1.06 |

TABLE 23

Stability studies in an argon atmosphere for the film formulations of Trial 13 at Time 6 months for the following conditions: 25° C. and 60% RH; 30° C. and 75% RH, 40° C. and 75% RH.

| | ENALAPRIL FILM Trial 13 | | | | | |
|---|---|---|---|---|---|---|
| | 1.25 mg | | | 2.5 mg | | |
| T = 6 months | 25° C. | 30° C. | 40° C. | 25° C. | 30° C. | 40° C. |
| Impurity C | 0.64 | 0.80 | 0.79 | 0.66 | 0.92 | 0.87 |
| Impurity B | — | — | — | — | — | — |
| Impurity H | 0.05 | 0.05 | 0.05 | 0.05 | 0.05 | 0.05 |
| Impurity D | 0.14 | 0.21 | 0.20 | 0.14 | 0.22 | 0.21 |
| Unknown | 0.23 | 0.34 | 0.34 | 0.23 | 0.39 | 037 |
| Unknown | — | — | — | — | — | — |
| Total | 1.06 | 1.40 | 1.38 | 1.06 | 1.40 | 1.38 |

Taken together all the data the formulation of Trial 13 is the optimum for production of films with 1.25 mg and 2.5 mg strengths.

Several embodiments of the present invention have been described. Nevertheless, it will be understood that various modifications may be made without departing from the spirit and scope of the invention. Accordingly, other embodiments are within the scope of the following claims.

What is claimed is:

1. An orodispersible film dosage form, comprising Enalapril or a pharmaceutically acceptable salt thereof and at least one water-soluble polymer and an effective amount of a pH increasing agent, wherein the water soluble polymer is a combination of pullulan and modified starch in an amount of from 55 to 75% w/w of the total weight of the film, wherein the ratio between pullulan and modified starch is from 1:1 to 1:2, and wherein the orodispersible film dosage form disintegrates within less than two minutes when placed onto a tongue.

2. The orodispersible film according to claim 1, wherein the pH increasing agent is NaOH at a concentration from 1 to 3% w/w of the total weight of the film.

3. The orodispersible film according to claim 1, wherein the pH of the film is from 6.4 to 6.5.

4. The orodispersible film according to claim 1, further comprising a plasticizing agent, a surfactant and a sweetener.

5. The orodispersible film according to claim 4, wherein the plasticizing agent is glycerol, the surfactant is polysorbate 80 and the sweetener is sucralose.

6. The orodispersible film according to claim 5, wherein the glycerol is at a concentration from 5 to 10% w/w; the polysorbate 80 is at a concentration from 4 to 6% w/w; and the sweetener is at a concentration from 4 to 7% w/w of the total weight of the film.

7. The orodispersible film according to claim 5, wherein the orodispersible film may comprise at least one further additive selected from the group consisting of a filler, a second sweetener, an acidic agent, a flavor, an emulsifier, an antioxidant, a pigment and a cooling agent.

8. The orodispersible film according to claim 1, wherein the size of the film is from 1 to 10 cm$^2$.

9. A process of manufacturing an orodispersible film, comprising the following steps:

Dispensing and weighing raw materials;

Mixing Enalapril maleate, a combination of water-soluble polymers, a pH increasing agent, a surfactant, a plasticizing agent, a sweetener and water under a nitrogen blanketing in a vacuum mixer until a homogenous casting solution has been formed;

Casting the solution on a one-sided PE/silicon coated paper and drying the solution at 40° C. for 4 hours;

Cutting and converting reels of film into single dose sachets;

Packaging sachets into a secondary laminated foil packaging with a different color according to dosage strength; and wherein the orodispersible film comprises Enalapril or a pharmaceutically acceptable salt thereof and at least one water-soluble polymer and an effective amount of a pH increasing agent, wherein the water soluble polymer is a combination of pullulan and modified starch in an amount of from 55 to 75% w/w of the total weight of the film, and wherein the ratio between pullulan and modified starch is from 1:1 to 1:2.

10. A method of treating hypertension in a pediatric population comprising administering the orodispersible films of claim 1.

11. The method of claim 10 wherein the pediatric population is from 1 to 18 years of age.

12. The method of claim 10 wherein the orodispersible film is administered to the patient in need thereof in an amount of not more than 0.5 mg/kg of weight.

* * * * *